US012376811B1

(12) United States Patent
Litzenberger

(10) Patent No.: US 12,376,811 B1
(45) Date of Patent: Aug. 5, 2025

(54) PORTABLE C-ARM WITH ATTACHABLE CONTROL STAND

(71) Applicant: CARESTREAM HEALTH, INC., Rochester, NY (US)

(72) Inventor: Michael A. Litzenberger, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 286 days.

(21) Appl. No.: 18/192,216

(22) Filed: Mar. 29, 2023

Related U.S. Application Data

(60) Provisional application No. 63/327,011, filed on Apr. 4, 2022, provisional application No. 63/327,006, filed on Apr. 4, 2022, provisional application No. 63/327,016, filed on Apr. 4, 2022.

(51) Int. Cl.
*A61B 6/00* (2024.01)

(52) U.S. Cl.
CPC .......... *A61B 6/4441* (2013.01); *A61B 6/4405* (2013.01)

(58) Field of Classification Search
CPC ............................. A61B 6/4441; A61B 6/4405
See application file for complete search history.

(56) References Cited

U.S. PATENT DOCUMENTS

2016/0296185 A1 * 10/2016 Gemmel ................ A61B 6/547

* cited by examiner

*Primary Examiner* — Mark D Remaly

(57) ABSTRACT

A C-arm radiographic imaging system for capturing radiographic images of an object has a wheeled base for transporting the system. A separate wheeled control stand is digitally and communicatively coupled to the C-arm. The control stand includes at least one monitor for displaying a GUI configured to provide operational controls for a user to operate the C-arm radiographic imaging system. The control stand is configured to straddle a lower end of the C-arm in a docked configuration to enable the C-arm, the wheeled base and the control stand to be rollably transported as a unit.

18 Claims, 2 Drawing Sheets

PORTABLE C-ARM WITH ATTACHABLE CONTROL STAND

CROSS REFERENCE TO RELATED APPLICATIONS

This application claims priority to U.S. Patent Application Ser. No. 63/327,006, filed Apr. 4, 2022, in the name of Zacks et al., and entitled ARTICULATING ARM FOR PORTABLE C-ARM WITH ATTACHABLE MONITOR CART; U.S. Patent Application Ser. No. 63/327,011, filed Apr. 4, 2022, in the name of Zacks et al., and entitled INTERCHANGEABLE DETECTORS ON PORTABLE C-ARM AND WORKING AREA LIGHTING; and U.S. Patent Application Ser. No. 63/327,016, filed Apr. 4, 2022, in the name of Zacks et al., and entitled C-ARM SYSTEM, all of which are hereby incorporated by reference herein in their entirety.

BACKGROUND OF THE INVENTION

The subject matter disclosed herein relates to mobile C-arm x-ray systems.

Currently, mobile C-arm radiographic imaging systems utilize several types of structures to support and enable the imaging structure (C-shaped arm, detector, and radiation source) to move horizontally. The most common arrangement of support structure is a horizontally translating boom that primarily travels in a direction perpendicular to the front of a mobile cart. The boom may be connected to a rotating element, which has a limited amount of rotational travel to keep the center of mass of the imaging structure within a designated range to ensure stability of the apparatus. The rotating element, in turn, is connected to the mobile C-arm cart. In this arrangement, the imaging structure may be translated horizontally and rotated about a vertical axis at the same time, to enable an imaging region between the source and detector to be selectively moved. This motion changes the orientation of the source and detector with respect to the patient.

C-arm x-ray systems may include a separate mobile control stand that is transported with the C-arm cart and stored as two individually movable components. When a C-arm unit needs to be transported from one room to another or from a storage location to a room, there are several options: a person may make two separate trips to transport the two components; two persons can each move one component; or a person can push one component and pull the second component at the same time. The first two options take additional personnel or additional time, while the third option can be physically dangerous to the person or could result in component damage if the person loses control of one of the components. When these two components are stored, they may be parked next to each other and occupy a large amount of space.

The discussion above is merely provided for general background information and is not intended to be used as an aid in determining the scope of the claimed subject matter.

BRIEF DESCRIPTION OF THE INVENTION

A C-arm radiographic imaging system for capturing radiographic images of an object has a wheeled base for transporting the system. A separate wheeled control stand is digitally and communicatively coupled to the C-arm. The control stand includes at least one monitor for displaying a GUI configured to provide operational controls for a user to operate the C-arm radiographic imaging system. The control stand is configured to straddle simultaneously the wheeled base and a lower end of the C-arm in a docked configuration to enable the C-arm, the wheeled base and the control stand to be rollably transported as a unit. An advantage that may be realized in the practice of some disclosed embodiments of the mobile C-arm radiographic imaging system is easier maneuverability and positioning of the system.

In one embodiment, a radiographic imaging system having a rigid support arm for securing an x-ray source and an x-ray detector in a fixed spatial relationship relative to each other includes a wheeled base attached to the rigid support arm for transporting the rigid support arm and a wheeled control stand electrically coupled to the x-ray source and the x-ray detector. The wheeled control stand is configured to control operations of the radiographic imaging system and to compactly straddle a lower end of the rigid support arm for rollably transporting the rigid support arm, the wheeled base and the wheeled control stand simultaneously as a unit.

In one embodiment, a radiographic imaging system for capturing radiographic images of an object includes a rigid support arm comprising an x-ray source and a digital radiographic (DR) detector secured in a fixed spatial relationship relative to each other, a wheeled base attached to the rigid support arm, and a wheeled control stand electrically coupled to the x-ray source and the DR detector. The wheeled control stand has a processing system configured to control operations of the radiographic imaging system, and is configured to straddle a lower end of the rigid support arm for rollably transporting the rigid support arm, the wheeled base and the wheeled control stand simultaneously as a unit.

One embodiment disclosed herein includes a mobile control stand configured to be attached to the mobile C-arm cart in such a way that they may be transported as a single unit. The cart and mobile control stand could be attached quickly and securely. A single person could move the two components simply without the possibility of losing control of the components. In one embodiment, a relief in the bottom of the mobile control stand allows the source end of the C-arm to pass through the open relief area. The mobile control stand includes attachment features to securely attach it to the C-arm cart. This combination of two components occupies a dimension equal to the C-arm alone. Since both the control stand and the C-arm unit are on casters, wheels, or are otherwise rollable, the two components could be moved in any direction while they are attached. This would also allow them to be translated sideways when stored.

When docked to the C-arm cart, the mobile control stand may be electrically connected to the C-arm cart. These connections may provide power, component communication and data transfer. When docked to the C-Arm cart, the entire control stand or a portion of the control stand may be elevated to raise its wheels off the ground. The elevation mechanism may be a component of the C-Arm cart or the control stand.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
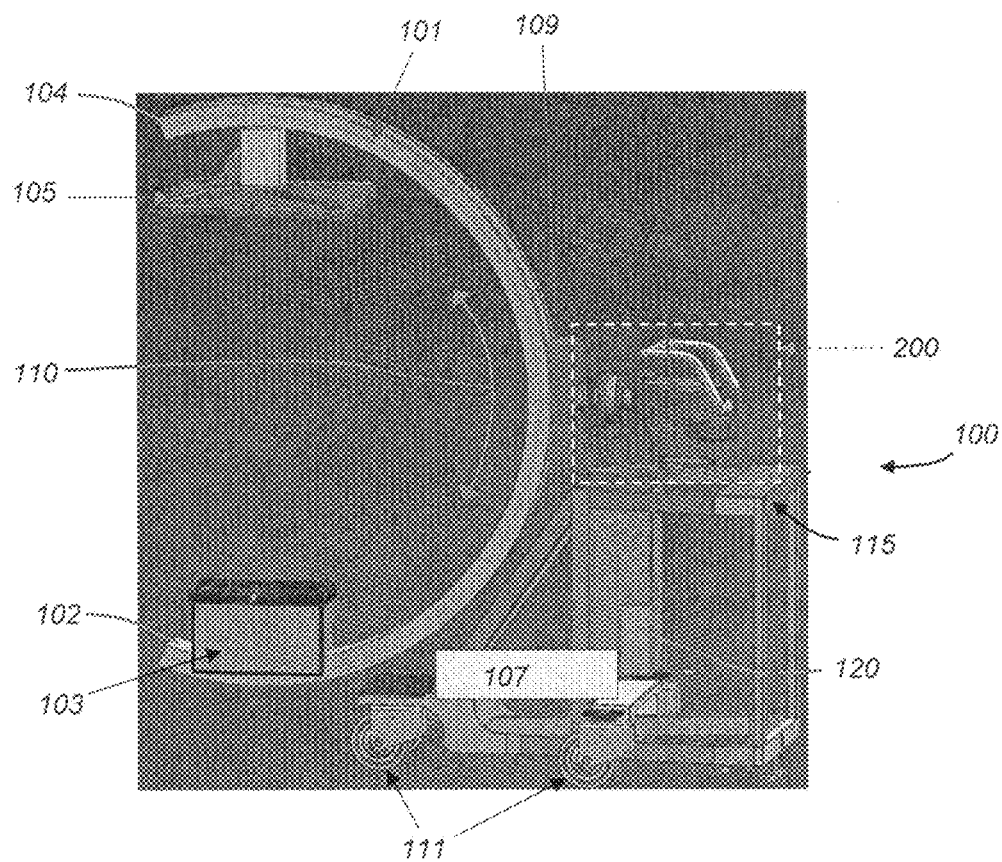
FIG. 1 is a perspective view of an exemplary mobile C-arm imaging system.

FIG. 1 is a perspective view of a mobile C-arm x-ray system 100, which includes a rigid, arc shaped support arm 101 having a first end 102 with an x-ray source assembly 103 affixed thereto, and a second end 104 having a digital radiographic (DR) detector 105 affixed thereto. The x-ray source assembly 103 is fixed in a position to emit an x-ray beam toward the DR detector 105. The x-ray source assembly 103 may include an adjustable collimator that controls a size and shape of the emitted x-ray beam. A patient positioned between the x-ray source assembly 103 and the DR detector 105 may be exposed to an x-ray beam emitted by the x-ray source assembly 103 and a radiographic image of the patient may be captured in the DR detector 105. Such a patient is typically lying on a patient bed that is configured to be positioned between the x-ray source assembly 103 and the DR detector 105. The support arm 101 is attached to a mobile cart 107 using a driver 109 and an articulating arm 200. The driver 109 may be motorized and configured to translate the support arm 101 relative to the driver 109 along both directions indicated by the arrow 110. The driver 109 may be used for moving and positioning the source assembly 103 and detector 105, as desired. Wheels 111 attached to a bottom side of the mobile cart 107 and a handle bar 115 are provided for an operator O (FIG. 3) to manually, rollably push and pull the mobile C-arm x-ray system 100 to any location as desired. A control system 120 may include a processing system in electrical and digital communication with the x-ray source assembly 103 and the DR detector 105 for controlling exposure procedures using the mobile C-arm x-ray system 100. The control system 120 may be used to initiate and control firing of the x-ray source in synchrony with an image capture phase of the detector 105, for example. Electronic memory in control system 120 may be used to digitally communicate with the DR detector 105 to receive digital radiographic images captured by, and transmitted from, the DR detector 105.

Figure 2:
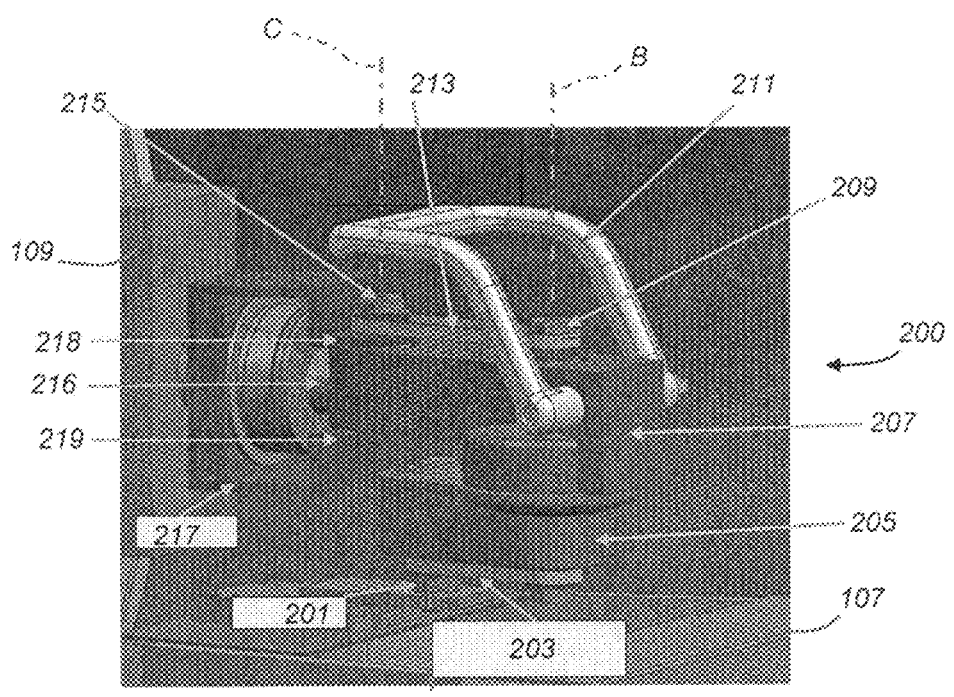
FIG. 2 is a perspective view of an exemplary articulating arm.

FIG. 2 is a perspective view of articulating arm 200 which connects the mobile cart 107 to the arc shaped support arm 101 via driver 109. Articulating arm 200 includes three rigid, rotatable segments each corresponding to a different one of three rotational axes. The first rigid segment 205 is connected to the mobile cart 107 by a bolt 201 extending therethrough. The bolt 201 is aligned coaxially with a first vertical rotational axis A, to allow the first rigid segment 205 to rotate about vertical rotational axis A relative to the mobile cart 107. The second rigid segment 207 is connected to the first rigid segment 205 by a bolt 209 extending therethrough. The bolt 209 is aligned coaxially with a second rotational axis B, to allow the second rigid segment 207 to rotate about vertical rotational axis B relative to the first rigid segment 205. The third rigid segment 217 is connected to the second rigid segment 207 by a bolt 215 extending therethrough. The bolt 215 is aligned coaxially with a third vertical rotational axis C, to allow the third rigid segment 217 to rotate about rotational axis C relative to the second rigid segment 207. The third rigid segment 217 is formed in the shape of a C having a top flange 218 secured to a top side of rigid segment 207 and a bottom flange 219 secured to a bottom side of rigid segment 207; both the top and bottom flanges are secured to rigid segment 207 using bolt 215. The third rigid segment 217 is fixed to the driver 109 by a bolt 216 extending therethrough. In one alternative embodiment, the distance between rotational axes B and C may be configured to be greater than the distance between rotational axes A and B. Hence, in this embodiment, axes A and C cannot coincide by manipulating rigid segments 205, 207, and 217.

In one alternative embodiment, synchronous elements 203 and 213 may be attached to the articulating arm 200 to limit angular rotation of rigid segments 205, 207, and 215 by providing a limiting detent mechanism against bolts 201, 209, 215, respectively. In addition, a brake mechanism within second rigid segment 207 may be activated by pivoting a manual lever 211, attached thereto, that locks in place and prevents rotation about either one or both of rotational axes B (first rigid segment 205 rotation relative to second rigid segment 207) and C (third rigid segment 217 rotation relative to second rigid segment 207).

Figure 3:
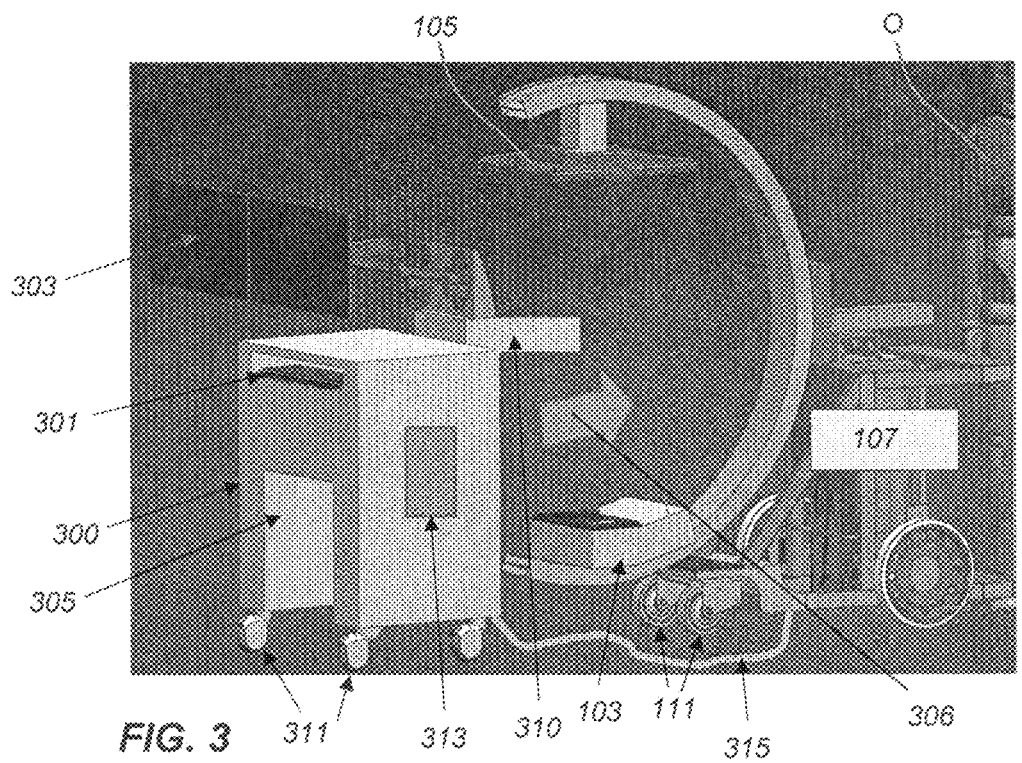
FIG. 3 is a perspective view of an exemplary mobile control stand and a mobile C-arm system.
Figure 4:
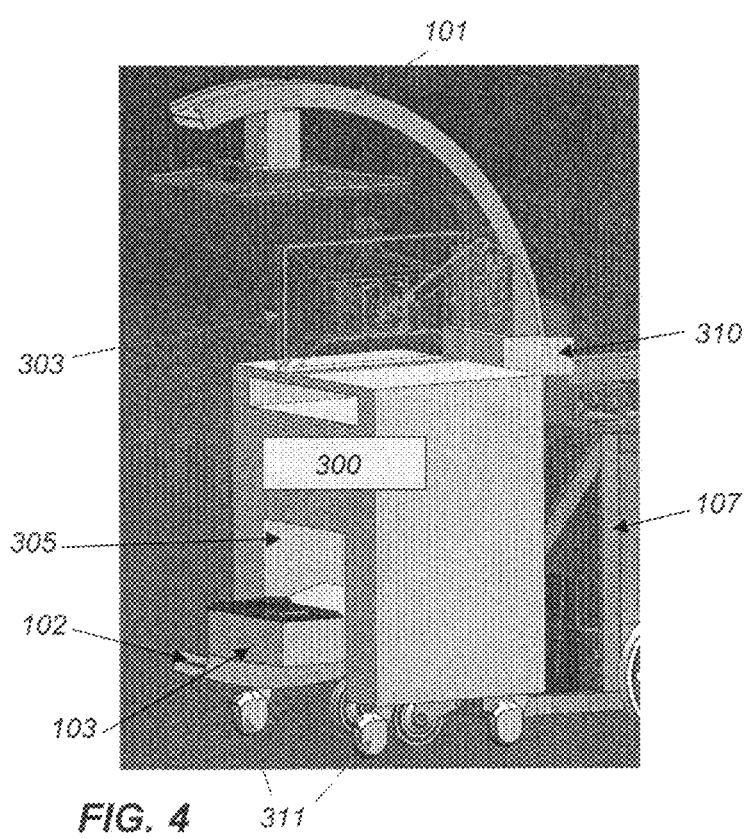
FIG. 4 is a perspective view of an exemplary mobile control stand docked to a mobile C-arm system.

Referring to FIG. 3 and FIG. 4, there is illustrated a mobile control stand 300 which may include a processing system 313, one or more data displays 303, a data and command input device 301, such as a keyboard or mouse, and wheels 311 for rollably transporting the mobile control stand 300. Recess 305 at the bottom side of mobile control stand 300 is configured to enable the mobile control stand 300 to be rolled toward the mobile cart 107, in the direction indicated by arrow 306, to pass over and straddle the lower end 102 of arc shaped support arm 101, the x-ray source assembly 103 attached thereto, and, as necessary, over the front wheels 111 of mobile cart 107. A latch portion 310 may be used to secure the mobile control stand 300 to mobile cart 107, which straddled configuration may be referred to herein as a docked position. Mobile control stand 300 may be electrically connected to mobile C-arm x-ray system 100 via connectable cable 315 which may be used to bidirectionally transmit control, power and data signals between mobile control stand 300 and mobile C-arm x-ray system 100. In another embodiment, mobile control stand 300 may communicate wirelessly with mobile C-arm x-ray system 100, under control by processing system 313, such as transmitting exposure control signals for firing the x-ray source, as needed, and for wirelessly receiving digital data from DR detector 105, such as radiographic images captured therein.

As shown in FIG. 4, mobile control stand 300 is in a docked position with mobile cart 107, whereby both mobile control stand 300 and the mobile cart 107 may be rollably transported as a unit by one person, and stored as a unit. FIG. 4 shows that at least a portion of the lower end 102 of arc shaped support arm 101 and the x-ray source assembly 103 extend beyond a front side of the mobile control stand 300. In the docked position, latch 310 secures together the mobile cart 107 and the mobile control stand 300.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Alternative Embodiments

C-arm radiographic imaging systems (C-arms) may be used for imaging in various scenarios. They can be moved toward and away from a patient bed/table for fluoroscopic imaging. During some procedures, it may be critical that the C-arm returns to the exact previous position so the image area is the same and the images can be usefully compared. Currently, operators may place marks or tape on the floor or table to mark the previous location and/or height of equipment. If the bed is moved, these locations may no longer be accurate. It's also important to know where the components of the C-arm are relative to the patient body.

One solution is to measure and record the position of the C-arm in space. This can be done in a number of ways, such as an RFID tag on the patient, an RFID tag on the bed, fiducials (such as visible light, IR, or ultrasound) on the patient which can be identified by a camera, fiducials on the bed, fiducials under the bed, two lasers pointing down on the floor; distance and angles of wheel movement and/or an accelerometer. Multiple fiducials (on the wall, on the bed, on the patient, etc.) will assist the system in knowing whether the bed or patient has moved. Two points on the bed and two spots on the C-arm are needed for triangulating the position. Another solution is to project the original image (camera or x-ray image) of where a region of interest (ROI) was on the patient or display, overlaying the current image of the area. This can be used for the C-arm position, the bed/table position and the patient position. In addition, having an indicator(s) on or near the detector to indicate the relative location of the equipment to the original ROI. This information can also be displayed to the operator via special glasses worn by the operator, as in an augmented reality system.

Current C-arms use x-ray technology for imaging a patient to assist in surgery and documentation. Using artificial intelligence (AI) and cameras, visual cues can be used to integrate the visual information with x-rays to provide more accurate and complete information to the doctor. Visual cues may include automatically determining anatomical region/body part, automatically determining body position, collimation level, movement (breath, etc.). One solution is to use smart technology to better enhance the information that the surgeon receives and assist them in giving the best care to their patients.

One solution is to use a camera to memorize the position, for example AP to lateral. This would help with projection angles and allow the operator to get the equipment back to the correct position. Another is to use an RGBD camera to estimate body part thickness to automatically set a better technique for x-ray exposure, since setting the technique based on simply choosing a body part may not get the best technique setting. A camera at the collimator allows the operator to make sure they are in the right spot before exposing the patient. Since the camera has a wider angle, it can give more detail about the collimated area and help the operator with a better starting point for imaging (which in turn reduces x-ray dose to the patient). Using this camera image will allow the system to set the collimator blades automatically for x-ray acquisition. When the equipment is moved from one projection to another, the field of view may need to change. The x-ray beam location can be set to match where the patient anatomy is; it will always apply the appropriate collimation for the body part and orientation. In addition, having a camera that senses movement, like breathing, is an asset in cardiac and vascular settings where tiny movements interfere with image accuracy and patient safety. Overlaying fluoroscopy images on RGB images or video may be helpful in a pain management setting. This would be especially helpful for vascular OBLs where there is no operator and the doctor needs to run things from table side. Augmented imaging can be used to overlay surgical navigation on the captured images showing the surgeon another view of the patient's anatomy during surgery and improving surgical accuracy.

Another procedure that may be desirable to integrate with x-ray imaging is synchronizing injections with the x-ray exposure. Starting the injection could trigger the x-ray exposure or the x-ray exposure could trigger the injection, such as contrast dye, and allow the doctor to follow its path. Current C-arms use x-ray technology for imaging a patient to assist in surgery and documentation. Each surgeon performs surgery in their own established way and have preferences for what images are captured, which as saved, how those images look/are processed, and what order the images are captured, for example.

One solution is that based on the procedure found for the patient by scanning the requisition/barcode, finding it on the worklist or entering it manually, the system will have patient information, what the procedure is and which surgeon is performing it. Based on the procedure and surgeon, the system will inform the operator what should be done next, such as the positioning of the equipment, and which image to take next. It can also automatically complete actions to assist the operator, for example, automatically processing the image in the way the surgeon prefers or automatically saving all images if the doctor always asks for all images to be saved. Since the system has the patient information, which may include weight, the system can automatically adjust the dose level based on the patient size and body part.

One solution is to use AI to learn common procedures and automatically adjust dose based on the procedure and projection. For example, as a number of surgeons take AP then lateral shots for a particular procedure, the system will use that information to set better generator techniques so the image is better and there is less chance of it having to be recaptured, thus increasing the image quality and mitigating dose. This can be done in a number of settings, such as pain management, pediatrics and spine (for example, ASC). A solution for assisting the operator to get the right content for the surgeon may be a customized profile that is automatically updated over time, if desired. For example, if a surgeon does a certain procedure consistently and 90% of the time they use low dose at a certain point in the procedure, the C-arm system could add this to their stored electronic profile. Some possible settings could be auto low dose, high level fluoroscopy settings, auto-pulse, and auto-save. These settings can be copied from one system to another, if desired so a surgeon can use any unit in their surgical case and their profile or settings are automatically used.

Another way of assisting the radiographer is if the operator is not familiar with the OR, a particular doctor or a specific procedure. There would be an application or guide on the system that would guide the operator as to to set up of the equipment in a particular room, the surgeon's preferences and/or workflow instructions on a particular procedure. Communication (communication and data exchange) between a c-arm system's components and accessories via short-range wireless technology standards can be enabled. In current systems, C-arm units are sold with separate monitor stands that need to communicate with each other and are linked by a wired connection. This system requires the monitor cart to be physically connected to the wall and the c-arm unit connected to the monitor cart so both can be powered.

One solution is to enable simple recognition, authentication and communication between C-arm system components and accessories via short-range wireless technology, such as Bluetooth, infrared, NFC or Wi-Fi, with connections initiated by various means, such as a key (for example an SD card), typing in a code, barcode scanner (for example a QR code or other barcode), a wired or wireless remote control or touching the components together. This partnering of components of the c-arm system will work whether the system has devices that only work with each other or a system that allows devices to be part of a pool. These devices may include, but are not limited to, C-arm unit, monitor cart, external monitor, foot pedals, remote exposure switch, tablet, on-bed controls, surgeon controls, headset, earbuds, microphone, speakers, detector and detector head. The short-range distance will allow a quick, reliable connection that is much less prone to errors connecting to the incorrect non-wired device. This will allow the quick and easy replacement of components and accessories that are not performing adequately or have been upgraded.

Currently, a radiographer is expected to follow the anatomy or contrast agent during a procedure. For new operators or operators not familiar with the area, this may be difficult. If the environment is distracting, the operator's ability to accomplish this may be impacted. One solution is a method for assisting the operator with following the desired path. Based on the anatomy and procedure, the operator can position the equipment at the initial point and the system can indicate what to do. The operator can choose two points and the system can provide the best path to follow. One solution would indicate the desired path graphically. Another solution may include haptic type feedback to help the radiographer understand that they are veering off the ideal path without pulling their attention from the patient. In addition, if the system knows the type of surgery and the position of the C-arm unit, it can guide the operator to the correct positioning for the best projection for the images needed. Once an image is captured, the system will use the image to figure out what the next step will be and indicate how to move the gantry from the current state to that next desired state. The initial and final position can be saved automatically so the operator could get back to the exact position at a later time during the procedure. This feature will be able to be turned off if desired.

Currently, C-Arm units that are sold with separate monitor stands are transported and stored as individual components but need to be used together. For example, a c-arm unit (A) purchased with a monitor stand (A) cannot be used with a different monitor stand (B). Additionally, a monitor stand (A) cannot be used with a different c-arm unit (B). There are several options to make sure this does not occur. The units and stands can be made to be identified as belonging together. They can be stored together which makes finding them easier when needed, but may take up space that is not easily available. Or they may be stored separately and when needed, each must be found so they can be used together. This option may help with finding locations for storage, but could require additional time to locate and retrieve the units for use. If one piece breaks down, both would be out of service until a repair is made. One solution is to allow the monitor cart to be used with any C-arm unit. In this case the person locating the equipment may use any available monitor cart with the C-arm unit. This will save time in critical situations. One solution is to have a "monitor on a stick" concept, where the monitor cart is simply a stand for the monitor(s) and potentially accessories, but the computing power is in the C-arm unit or an external to the monitor cart server which communicates with the monitor stand. This communication can be wired or wireless. This would allow the site to update their monitors as technology changes without needing to replace the entire unit. It will also allow working units to be used even if other elements are down/not available. This will also allow the C-arm unit to be used without the monitor cart and be powered directly (such as via the wall electrical outlet). Another solution is placing the PC in the monitor cart. In this case, there would be a method of marrying the monitor cart with any related C-arm unit.

In one embodiment, a C-arm radiographic imaging system includes an x-ray source and a digital radiographic detector for capturing radiographic images of a patient. A digital display may include a graphical user interface be presented on the display and an electronic memory having stored therein patient names, physician names, and various imaging procedures associated therewith. A processing system electrically connected to the digital display presents the GUI and receives user inputs via the GUI. The processing system outputs a preferred x-ray source and digital detector alignment and an imaging procedure in response to receiving a name of the patient and a physician name input by a user via the GUI. Thee processing system may also automatically position the x-ray source and the digital detector in a preferred alignment.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A C-arm radiographic imaging system for capturing radiographic images of an object, the system comprising:
    a C shaped arm comprising an x-ray source and a digital radiographic detector each attached to one of two opposing ends of the C shaped arm;
    a wheeled base attached to the C shaped arm for transporting the C shaped arm; and
    a wheeled control stand digitally and communicatively coupled to the C shaped arm, the wheeled control stand comprising at least one monitor for displaying a graphical user interface (GUI) configured to provide operational controls for a user to operate the C-arm radiographic imaging system,
    wherein the wheeled control stand is configured with a recessed opening at a bottom side of the wheeled control stand such that the wheeled control stand straddles one of the two opposing ends of the C shaped arm in a docked configuration to enable the C shaped arm, the wheeled base and the control stand to be rollably transported as a unit.

2. The system of claim 1, further comprising a latch to secure the control stand to the wheeled base.

3. The system of claim 1, wherein the wheeled control stand is further configured to also straddle a portion of the wheeled base, and wherein a forward portion of the straddled end of the C shaped arm extends further forward than the wheeled control stand in the docked configuration, and wherein a rearward portion of the wheeled base extends further rearward than the wheeled control stand in the docked configuration.

4. The system of claim 1, further comprising a handlebar for manually rollably transporting the C shaped arm, the wheeled base and the control stand as a unit.

5. The system of claim 1, wherein the handlebar is attached to the wheeled base.

6. A radiographic imaging system for capturing radiographic images of an object, the system comprising:
    a rigid support arm for securing an x-ray source and an x-ray detector in a fixed spatial relationship relative to each other;
    a wheeled base attached to the rigid support arm for transporting the rigid support arm; and
    a wheeled control stand electrically coupled to the x-ray source and the x-ray detector, the wheeled control stand configured to control operations of the radiographic imaging system,
    wherein the wheeled control stand is configured to compactly straddle a lower end of the rigid support arm in a docked configuration for rollably transporting the rigid support arm, the wheeled base and the wheeled control stand simultaneously as a unit.

7. The system of claim 6, further comprising a latch to secure the wheeled control stand to the wheeled base.

8. The system of claim 6, wherein a forward portion of the lower end of the rigid support arm extends further forward than the wheeled control stand in the docked configuration, and wherein a rearward portion of the wheeled base extends further rearward than the wheeled control stand in the docked configuration.

9. The system of claim 6, further comprising a handlebar for manually rollably transporting the rigid support arm, the wheeled base and the wheeled control stand as a unit.

10. The system of claim 9, wherein the handlebar is attached to the wheeled base.

11. The system of claim 6, wherein the wheeled control stand is configured with a recessed opening at a bottom side of the wheeled control stand such that the wheeled control stand compactly straddles the lower end of the rigid support arm in the docked configuration.

12. A radiographic imaging system for capturing radiographic images of an object, the system comprising:
    a rigid support arm comprising an x-ray source and a digital radiographic (DR) detector secured in a fixed spatial relationship relative to each other;
    a wheeled base attached to the rigid support arm for transporting the rigid support arm; and
    a wheeled control stand electrically coupled to the x-ray source and the DR detector, the wheeled control stand comprising a processing system configured to control operations of the radiographic imaging system, wherein the wheeled control stand is configured to straddle a lower end of the rigid support arm for rollably transporting the rigid support arm, the wheeled base and the wheeled control stand simultaneously as a unit.

13. The system of claim 12, further comprising a display attached to the wheeled control stand for displaying digital radiographic images captured by the DR detector, and for displaying a graphical user interface useable by an operator to control imaging operations of the radiographic imaging system.

14. The system of claim 12, further comprising a latch to secure the wheeled control stand to the wheeled base.

15. The system of claim 12, wherein a forward portion of the straddled lower end of the rigid support arm extends further forward than the wheeled control stand in a docked configuration, and wherein a rearward portion of the wheeled base extends further rearward than the wheeled control stand in the docked configuration.

16. The system of claim 12, further comprising a handlebar for manually rollably transporting the C shaped arm, the wheeled base and the control stand as a unit.

17. The system of claim 16, wherein the handlebar is attached to the wheeled base.

18. The system of claim 12, wherein the wheeled control stand is configured with a recessed opening at a bottom side of the wheeled control stand to straddle the lower end of the rigid support arm in a docked configuration.

* * * * *